United States Patent [19]

Toussaint et al.

[11] Patent Number: 5,037,793

[45] Date of Patent: Aug. 6, 1991

[54] CATALYST FOR THE HYDROGENATION OF UNSATURATED ALIPHATIC COMPOUNDS

[75] Inventors: Herbert Toussaint, Frankenthal; Juergen Schossig, Fussgoenheim; Heinz Graefje; Wolfgang Reiss, both of Ludwigshafen; Roland Spahl, Lorsch; Matthias Irgang, Heidelberg; Walter Himmel, Gruenstadt; Gerhard Koppenhoefer, Ludwigshafen, all of Fed. Rep. of Germany

[73] Assignee: BASF Aktiengesellschaft, Ludwigshafen, Fed. Rep. of Germany

[21] Appl. No.: 502,926

[22] Filed: Apr. 2, 1990

[30] Foreign Application Priority Data

Apr. 27, 1989 [DE] Fed. Rep. of Germany ....... 3913835

[51] Int. Cl.$^5$ .................... B01J 21/06; B01J 23/72; B01J 23/74; B01J 23/88
[52] U.S. Cl. .................................. 502/308; 502/331; 568/861
[58] Field of Search ..................... 502/331, 337, 308; 568/861

[56] References Cited

U.S. PATENT DOCUMENTS

| | | | |
|---|---|---|---|
| 2,953,605 | 9/1960 | Hort | 502/331 X |
| 3,449,445 | 6/1969 | Wetherill | 260/635 |
| 3,617,517 | 11/1971 | Rashkin | 502/308 X |
| 3,962,140 | 6/1976 | Alcorn et al. | 252/470 |
| 4,035,263 | 7/1977 | Umemura et al. | 252/459 |
| 4,048,116 | 9/1977 | Voges et al. | 252/470 |
| 4,072,714 | 2/1978 | Voges et al. | 260/584 R |
| 4,128,730 | 12/1978 | Reich | 502/331 X |
| 4,152,353 | 5/1979 | Habermann | 564/480 X |
| 4,287,099 | 9/1981 | Baer et al. | 252/465 |
| 4,384,147 | 5/1983 | Baer et al. | 568/861 |

FOREIGN PATENT DOCUMENTS

| | | |
|---|---|---|
| 18569 | 4/1982 | European Pat. Off. . |
| 0266727 | 5/1988 | European Pat. Off. . |
| 2536273 | 2/1977 | Fed. Rep. of Germany . |
| 2305230 | 10/1976 | France . |
| 2320776 | 3/1977 | France . |

*Primary Examiner*—W. J. Shine
*Attorney, Agent, or Firm*—John H. Shurtleff

[57] ABSTRACT

A catalyst for the hydrogenation of unsaturated aliphatic compounds having a content of 20–70% w/w of nickel oxide, 25–45% w/w of zirconium oxide and 5–40% w/w of copper oxide, based on the oxidic, unreduced catalyst.

4 Claims, No Drawings

10

CATALYST FOR THE HYDROGENATION OF UNSATURATED ALIPHATIC COMPOUNDS

The present invention relates to a novel catalyst for the hydrogenation of unsaturated aliphatic compounds, in particular for the hydrogenation of unsaturated alcohols and aldehydes, for example hydrogenation of but-2-ine-1,4-diol to 1,4-butanediol and from 2-ethylhexen-2-al to 2-ethylhexanol.

Numerous catalysts have been proposed for the hydrogenation of unsaturated aliphatic compounds. For example, U.S. Pat. No. 3,449,445 discloses that but-2-ine-1,4-diol can be hydrogenated to 1,4-butanediol in good yields when use is made of a catalyst containing nickel, copper and manganese on silicon dioxide. However, when 1,4-butanediol is prepared by this process on an industrial scale, deposition of silicon dioxide occurs in the heat exchangers and pipelines, and the removal of such deposits unavoidably constitutes a highly laborious procedure.

Good results are obtained when acetylenic alcohols are hydrogenated using the unsupported catalyst described in DE-OS 2,536,276, which contains the oxides of nickel, copper, molybdenum and manganese. When but-2-ine-1,4-diol is hydrogenated to 1,4-butanediol, particularly favorable results are achieved by intensifying the reaction conditions (high hydrogen pressure and high temperature) at the expense, however, of an unwanted formation of butanol. In addition, catalysts shaped by extrusion or pelleting are not dimensionally stable under large-scale production conditions and quickly disintegrate.

According to EP 0,018,569, particularly desirable results are achieved in the hydrogenation of but-2-ine-1,4-diol using a hydrogenation catalyst containing oxides of the metals nickel, copper, molybdenum and manganese, when said catalyst has been prepared by precipitation of the metal salts, filtration, washing, drying and tempering, with the addition of a salt of aluminum or iron prior to the precipitation stage. However, when this catalyst is used industrially over long on-stream periods, slow but steady disintegration thereof occurs.

There has thus been a need to provide a catalyst which is suitable for use in the hydrogenation of unsaturated aliphatic compounds and which does not suffer from the above limitations. To be advantageous, such a novel catalyst must satisfy the following requirements: a) high stability—an important feature for continuous industrial operation, and b) improved catalyst activity.

We have now found a catalyst which is suitable for use in the hydrogenation of unsaturated aliphatic compounds and which meets the above requirements to a high degree. The catalyst, which contains nickel and copper, is characterized by a content of 20-75% of nickel oxide, 10-75% of zirconium dioxide and 5-50% of copper oxide, by weight of the oxidic, unreduced catalyst.

Our novel catalyst is exceptionally well-suited for the hydrogenation of unsaturated aliphatic compounds, examples of which are olefinic and acetylenic hydrocarbons, which may be substituted by, for example, hydroxy or aldehyde groups, such as the industrially important compounds but-2-ine-1,4-diol, but-2-ene-1,4-diol and 2-ethyl-2-hexenal.

In its oxidic, unreduced form, the catalyst of the invention has, for example, the following composition: from 30 to 70%, preferably from 40 to 60% and more preferably from 35 to 55% w/w of nickel oxide, from 10 to 60%, preferably from 15 to 50% and more preferably from 25 to 45% w/w of zirconium dioxide, and from 5 to 40%, preferably from 10 to 35% and more preferably from 5 to 20% w/w of copper oxide. The catalyst may also contain, for example, from 0.1 to 5% w/w of molybdenum oxide and, for example, from 0 to 10% w/w of manganese oxide.

Our novel catalyst is particularly well-suited for the hydrogenation of but-2-ine-1,4-diol to 1,4-butanediol, in which case it makes considerably longer on-stream periods possible and increases the throughput significantly.

Our novel catalyst may be prepared, for example, by conventional precipitation of salts of the metals nickel, copper, zirconium and, if required, manganese from an aqueous solution at a temperature of from 30° to 90° C. and a pH of from 5 to 9, and filtration of the suspension, after which the filter cake is dried and then tempered at a temperature of from 300° to 700° C. The molybdenum is added in the form of ammonium heptamolybdate prior to the drying stage. Precipitation is effected by mixing an aqueous solution of salts, such as the nitrates, sulfates or acetates, of the metals nickel, copper, zirconium and, possibly, manganese with an aqueous solution of an alkali metal carbonate. The proportions of the metal salts are adjusted so as to give the aforementioned composition of the catalyst after tempering.

According to an advantageous embodiment of the preparation process, a portion of, say, up to 50% w/w of the water-soluble zirconium salt, based on the zirconium used, is replaced by solid zirconium dioxide, which is either added to the aqueous metal salt solution prior to precipitation or is placed in the reaction vessel at the commencement of the process.

More specifically, the catalyst is prepared, for example, by stirring the aqueous solution of the metal salts together with an aqueous alkali metal carbonate solution, preferably a sodium carbonate solution, to cause precipitation of the metals in the form of a mixture of their hydroxides and carbonates. The concentration of metal salts in the metal salt solution is advantageously 30 to 40%. The aqueous alkali metal carbonate solution has a concentration of, say, from 10 to 20% and preferably from 15 to 20% w/w. Precipitation is carried out at a temperature of from 30° to 90° C. and preferably from 70° to 90° C. and at a pH of from 7 to 9.

The resulting suspension is filtered, and the filter cake is washed with water until free from anions. It is then dried at, say, from 120° to 200° C., in a drying cabinet or spray drier. Preferably, the molybdenum is added to the moist filter cake in the form of ammonium heptamolybdate. The dried filter cake is tempered at a temperature of from 350° to 700° C., preferably from 400° to 600° C.

It is advantageous to shape the resulting catalyst composition before use by known pelleting or extrusion methods. For example, it can be pressed to pellets measuring 6×3 mm using a pelleting aid, preferably graphite. The pellets thus formed are tempered at a temperature of from 300° to 700° C., preferably from 400° to 600° C. The pellets have a loose weight of from 1,500 to 1,900 g/l, a porosity (as determined by water absorption) of from 0.2 to 0.4 ml/g and a hardness of 3,000 to 4,000 N/cm². Before it is used for the purpose of the invention, the catalyst thus obtained is subjected to reductive treatment with hydrogen at a temperature of from 200° to 350° C., preferably from 230° to 280° C., for example for a period of from 20 to 40 hours under a hydrogen pressure of from 1 to 300 bar and preferably from 100 to 150 bar.

Hydrogenation of the aforementioned unsaturated compounds using our novel catalyst is carried out, for example, at temperatures ranging from 40° to 200° C. and under pressures ranging from 30 to 320 bar using a gas containing hydrogen. The hydrogenation of but-2-ine-1,4-diol to 1,4-butanediol, which is of particular commercial importance, is carried out continuously, in known manner, in a reactor containing the catalyst in the form of a fixed bed. As is evident from the Examples below, considerably longer onstream periods and higher throughputs are achieved than is the case when conventional catalysts are used.

We have found that the catalyst of the invention also possesses the following surprising advantage: after deactivation thereof, which occurs only after very long on-stream periods, the catalyst can be virtually completely reactivated by treatment with water for from 8 to 48 hours at a temperature of from 100° to 250° C. and under a pressure of from 100 to 320 bar.

EXAMPLES

In the following Examples, the percentages are by weight.

EXAMPLE 1 a) Preparation of the catalyst

An aqueous solution of nickel nitrate, copper nitrate and zirconium acetate containing 4.48% of NiO, 1.52% of CuO and 2.82% of $ZrO_2$ was fed at a steady rate to a stirred vessel together with a 20% aqueous sodium carbonate solution at a temperature of 70° C. such that a pH of 7.0 was maintained (as measured with a glass electrode), to effect precipitation.

The resulting suspension was filtered, and the filter cake was washed with completely demineralized water until the electrical conductivity of the filtrate was approx. 20 uS. Ammonium heptamolybdate was then added to the moist filter cake in an amount adjusted to give the oxide mixture stated below. The filter cake was then dried at a temperature of 150° C. in a drying cabinet or spray drier. The hydroxide/carbonate mixture thus obtained was then tempered at a temperature of 500° C. for a period of 4 hours.

The resulting catalyst had the following composition: 50% NiO, 17% CuO, 1.5% $MoO_3$ and 31.5% $ZrO_2$. The powdered catalyst was mixed with graphite and pressed to pellets measuring 6×3 mm. These pellets had a porosity (as determined by water absorption) of 0.20 ml/g and a hardness of 3,500 $N/cm^2$.

b) Hydrogenation of but-2-ine-1,4-diol

The catalyst obtained as described in a) above was reduced in a hydrogenation reactor at a temperature of 250° C. and under a hydrogen pressure of 150 bar. At a temperature of 150° C. and a hydrogen pressure of 250 bar, 5 parts by weight of a 50% aqueous solution of but-2-ine-1,4-diol were hydrogenated with 2,500 parts by volume (STP) of hydrogen in contact with 8 parts by volume of the catalyst, per hour. The feed of butinediol was diluted with 50 parts by volume per hour of recycled effluent in order to control the temperature in the reactor and establish the correct distribution of liquid across the catalyst bed. The heat of hydrogenation was removed via a heat exchanger installed in the liquid circuit. The excess gas obtained following separation of the gas phase from the liquid phase was replenished with fresh hydrogen and recycled to the reactor inlet.

The conversion of but-2-ine-1,4-diol was virtually 100%. By-products of the hydrogenation were, for example:

| | |
|---|---|
| butanol | <5% w/w |
| 2-methyl-1,4-butanediol | <0.2% w/w |
| but-2-ene-1,4-diol | <0.1% w/w |
| [2-(4-hydroxy)butoxy]oxalene | <0.3% w/w |
| 4-hydroxybutyraldehyde | <0.5% w/w |
| gamma-butyrolactone | <0.5% w/w |

(percentages based on anhydrous contents)

In order to effect further conversion of the last four partially hydrogenated compounds in the above list, the effluent mixture was passed once through a second hydrogenation stage containing the same catalyst, where it was post-hydrogenated at a temperature of 180° C. and under a hydrogen pressure of 250 bar.

The resulting product contained at least 94% w/w of 1,4-butanediol (based on anhydrous content) and was purified by distillation to give pure 1,4-butanediol. No distinct diminution of pressure was evident after an on-stream period of 4 months, when still no catalyst components were found in the mixture discharged from the reactor. Throughputs of butinediol were achieved which were three times higher than that obtained in the comparative test c) described below.

c) Comparative Test

The hydrogenation described in b) above was repeated using the catalyst described in the Example of EP-PS 18,569. After only a few weeks on stream, it was necessary to remove the catalyst bed due to clogging.

EXAMPLE 2

The hydrogenation described in Example 1, section b) was continued for a longer period of time. After an on-stream time of about 3 months it became evident that the catalyst of the invention was losing hydrogenating efficiency, this being chiefly due to deposits of inorganic components derived from the industrial butinediol solution used. The catalyst bed was flushed for 24 hours with condensate having a temperature of 200° C. This treatment restored the catalyst to virtually its original activity. The flushing water contained traces of zirconium dioxide and also, for example, 0.1% w/w of silicon, 0.03% w/w of sodium, 0.01% w/w of copper, and organic components (<5% w/w).

EXAMPLE 3

Hydrogenation of 2-ethylhexen-2-al

A continuous high-pressure reactor was packed with the catalyst prepared as described in Example 1, section a). Reduction of the oxidic catalyst was carried out at a temperature of 270° C. and under a hydrogen pressure of 150 bar. 3 Parts by volume of 2-ethylhexen-2-al (purity: 95-96% w/w) were hydrogenated in contact with 1.5 parts by volume of the reduced catalyst at a temperature of 140° C. and under a hydrogen pressure of 250 bar, per hour. The fresh supply was diluted with 30 parts/h of effluent for the reasons given in Example 1, section b). The unconsumed hydrogen leaving the hydrogenation was replenished with fresh hydrogen and recycled. Conversion was virtually quantitative. The discharged product contained, for example, the following components:

| | |
|---|---|
| 2-ethylhexen-2-al | ≦0.01% w/w |
| 2-ethylhexanal | <0.03% w/w |
| 2-ethylhexanol | >95.9% w/w |

As was to be expected, reducing the pressure lowered the hydrogenating efficiency. At a pressure of 40 bar, it was still possible to hydrogenate 0.5 part by volume per hour of 2-ethylhexen-2-al whilst maintaining the above discharge specification. There was no instance of dissolved or undissolved catalyst components being contained in the products discharged.

The throughput rates achieved are about six times higher than those obtained when using conventional nickel-on-silicon dioxide catalysts.

The 2-ethylhexanol obtained by distillation of the crude hydrogenated product is distinguished by a high degree of purity. Worthy of particular note is its low sulfuric acid color index of 5 ALPHA, which is not reached when 2-ethyl-hexen-2-al is hydrogenated to 2-ethylhexanol with the aid of the normally used nickel-on-silicon dioxide catalyst.

We claim:

1. A catalyst for the hydrogenation of unsaturated aliphatic compounds which has a content of from 20% to 70% w/w of nickel oxide, from 25% to 45% w/w of zirconium dioxide and from 5% to 40% w/w of copper oxide, based on the oxidic, unreduced catalyst.

2. A catalyst for the hydrogenation of unsaturated aliphatic compounds which as a content of from 40% to 60% w/w of nickel oxide, from 25% to 45% w/w of zirconium dioxide and from 10% to 35% w/w of copper oxide, based on the oxidic, unreduced catalyst.

3. A catalyst for the hydrogenation of unsaturated aliphatic compounds which has a content of from 35% to 55% w/w of nickel oxide, from 25% to 45% w/w of zirconium dioxide, from 5% to 20% w/w of copper oxide and from 0.1% to 5% w/w of molybdenum oxide, based on the oxidic, unreduced catalyst.

4. A catalyst as claimed in claim 1, wherein the nickel oxide content is from 30% to 70% w/w, based on the oxidic, unreduced catalyst.

* * * * *

UNITED STATES PATENT AND TRADEMARK OFFICE
CERTIFICATE OF CORRECTION

PATENT NO. : 5,037,793

DATED : August 6, 1991

INVENTOR(S) : Toussaint et al

It is certified that error appears in the above-identified patent and that said Letters Patent is hereby corrected as shown below:

In Claim 2, at column 6, line 10: change "as a content" to correctly read --has a content--.

Signed and Sealed this

Twenty-ninth Day of December, 1992

Attest:

DOUGLAS B. COMER

*Attesting Officer*     *Acting Commissioner of Patents and Trademarks*